US009228935B2

(12) United States Patent
Petrich et al.

(10) Patent No.: US 9,228,935 B2
(45) Date of Patent: Jan. 5, 2016

(54) DEVICE FOR DETECTING AN ANALYTE IN A BODILY FLUID

(71) Applicant: Roche Diagnostics Operations, Inc., Indianapolis, IN (US)

(72) Inventors: Wolfgang Petrich, Bad Schönborn (DE); Frank Weidner, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 361 days.

(21) Appl. No.: 13/745,371

(22) Filed: Jan. 18, 2013

(65) Prior Publication Data

US 2013/0126712 A1  May 23, 2013

Related U.S. Application Data

(63) Continuation of application No. PCT/EP2011/061783, filed on Jul. 11, 2011.

(30) Foreign Application Priority Data

Jul. 20, 2010  (EP) .................................... 10170088

(51) Int. Cl.
*G01N 21/17* (2006.01)
*G01N 21/84* (2006.01)
*G01N 21/78* (2006.01)

(52) U.S. Cl.
CPC ............ *G01N 21/17* (2013.01); *G01N 21/8483* (2013.01); *G01N 21/78* (2013.01); *G01N 2201/0221* (2013.01)

(58) Field of Classification Search
CPC ... G01N 21/17; G01N 21/78; G01N 21/8483; G01N 2201/0221
See application file for complete search history.

(56) References Cited

U.S. PATENT DOCUMENTS 5,083,214 A  1/1992  Knowles
5,614,744 A  3/1997  Merrill
(Continued)

FOREIGN PATENT DOCUMENTS

DE  196 31 086 A1  2/1997
EP  1 351 189 A1  10/2003
(Continued)

OTHER PUBLICATIONS

English translation of International Preliminary Report on Patentability, PCT/EP2011/061783, Feb. 28, 2013.
M. Castaing, C. Hohl, C. Horauf, E. Rohlack, C. Vrancic, F. Weidner and W. Petrick; "Nanoliter Sample Analytics (NSA)," Roche Diagnostics GmbH, 2009.
(Continued)

*Primary Examiner* — Francis M Legasse, Jr.
(74) *Attorney, Agent, or Firm* — Bose McKinney & Evans LLP

(57) ABSTRACT

A device is proposed for detecting at least one analyte in a bodily fluid. The device comprises at least one test element with at least one two-dimensional evaluation region. The device furthermore comprises at least one spatially resolving optical detector having a plurality of pixels. The detector is designed to image at least part of the test element onto an image region. In the process, at least part of the evaluation region is imaged onto an evaluation image region. The detector is matched to the test element such that a predetermined minimum number of pixels is provided for each dimension within the evaluation image region. The pixels are arranged in a two-dimensional matrix arrangement. The matrix arrangement has pixel rows and pixel columns, wherein the pixel rows are arranged substantially parallel to a longitudinal direction of the evaluation region and/or of the evaluation image region.

52 Claims, 5 Drawing Sheets

(56) References Cited

U.S. PATENT DOCUMENTS

| | | |
|---|---|---|
| 6,249,593 B1 | 6/2001 | Chu et al. |
| 6,515,702 B1 | 2/2003 | Yadid-Pecht et al. |
| 6,847,451 B2 * | 1/2005 | Pugh .............................. 356/436 |
| 7,344,081 B2 | 3/2008 | Tseng |
| 7,889,329 B2 | 2/2011 | Petrich et al. |
| 8,293,539 B2 | 10/2012 | Petrich et al. |
| 2003/0123087 A1 | 7/2003 | Sakai et al. |
| 2003/0206302 A1 | 11/2003 | Pugh |
| 2004/0095360 A1 | 5/2004 | Tseng et al. |
| 2005/0013494 A1 | 1/2005 | Srinivasan et al. |
| 2007/0046803 A1 | 3/2007 | Ahn |
| 2010/0288060 A1 * | 11/2010 | Ronsick et al. ............ 73/864.63 |

FOREIGN PATENT DOCUMENTS

| | | |
|---|---|---|
| EP | 1 359 409 A2 | 11/2003 |
| EP | 1 582 598 A1 | 10/2005 |
| EP | 1843 148 A1 | 10/2007 |
| EP | 2 151 686 A1 | 2/2010 |
| JP | 2003-284700 A | 10/2003 |
| WO | WO 2009/148624 A1 | 12/2009 |
| WO | WO 2010/055308 A1 | 5/2010 |

OTHER PUBLICATIONS

W. Petrich, "Photometric System (PMS)," Roche Diagnostics GmbH, 2006. (No English Translation).

* cited by examiner

DEVICE FOR DETECTING AN ANALYTE IN A BODILY FLUID

RELATED APPLICATIONS

This application is a continuation of PCT/EP2011/061783, filed Jul. 11, 2011, which claims priority to EP 10 170 088.8, filed Jul. 20, 2010 both of which are hereby incorporated by reference in their entireties.

BACKGROUND

This disclosure relates to a device for detecting at least one analyte in a bodily fluid by means of at least one test element and preferably by means of at least one lancet with a capillary. This disclosure furthermore relates to a method for recognizing an evaluation region of a device for detecting at least one analyte in a bodily fluid. Such devices and methods are used, in particular, in diagnostics for qualitatively or quantitatively detecting one or more analytes, for example one or more metabolites such as e.g. blood glucose, in bodily fluids such as e.g. blood or interstitial fluid.

The prior art has disclosed a multiplicity of devices for detecting at least one analyte in a bodily fluid. Here, use is generally made of test elements which have at least one test chemical. This test chemical contains at least one detection reagent which, when it comes into contact with the at least one analyte, carries out an analyte-specific reaction, which can for example be detected by electrochemical and/or optical means.

In addition to individual systems, in which the sample of bodily fluid is obtained and analyzed separately, integrated systems in particular have prevailed in recent times. By way of example, integrated systems for determining the blood glucose are composed of means for obtaining blood and means for determining glucose. In the step of obtaining blood, some systems make use of a flat lancet with a semi-open microcapillary, in which the capillary typically has a width of 120 μm and a length of 4 mm. After obtaining blood by means of a piercing process, for example into a finger tip, an ear lobe or a forearm, the blood taken up into the capillary is often transferred onto a test field of the test element by virtue of causing the lancet to approach said test field, for example by being pressed onto the latter. As a result, there likewise is the creation of an approximately 120 μm wide print of the capillary on the test element, for example a strip-shaped test element, which changes depending on the blood glucose content and depending on the test chemical recipe. In the case of optical systems, this change generally consists of a local change in color, which can be measured by reflectance photometry. In principle, details of this method are sufficiently well known from the literature.

Here, in principle, there is a problem in that measuring the discoloring of the test fields by means of non-spatially-resolved sensors, i.e. by means of for example a single photodiode, is problematic in that the position of the grayscale discoloring or discoloring on the test field in this case would have to be captured very precisely by mechanical means and with low mechanical and/or optical tolerances. This is difficult to achieve in the case of a lancet that can move for piercing and for obtaining blood. By way of example, if a tolerance in the lateral position of less than 10% is to be achieved, the positional tolerance in the case of a capillary with a width of 120 μm must not exceed approximately ±10 μm; this is a significant challenge from a mechanical point of view.

It is for this reason that the use of a spatially resolved detector, e.g. a CMOS camera, has been proposed a number of times. By way of example, U.S. Pat. No. 6,847,451 B1 describes devices and methods for determining the concentration of an analyte in a physiological sample. Here, use is made of at least one light source and at least one detector array, as well as of means for determining whether a sufficient amount of sample is present on a plurality of different surfaces. Inter alia, it is proposed here to use a CCD array as detector array. Alternatives to the spatially resolved detection include, for example, spatially resolved illumination or a mixture of such methods, such as e.g. methods based on line-by-line scanning.

U.S. Publication No. 2004/0095360 A1 describes a user interface of an image recording device and an image processing method which can for example be used to evaluate biological samples such as pregnancy tests or drugs tests. In the process, a high-resolution camera sensor, designed as a color sensor, is used for actually capturing the image. Inter alia, it is proposed here that use is made of a line and a reference line within the test.

U.S. Pat. No. 7,344,081 B2 describes a method for automatically recognizing a test result of a sample zone on a test strip. In the process, an image of a barcode and an image of at least one test strip are recorded. A color response of the test strip to a sample application is determined. However, in order to resolve a barcode, it is inherently necessary to use a detector with a high resolution and hence with a large number of pixels.

U.S. Pat. No. 5,083,214 describes a device and a method for determining suitable points to take a sample. In the process, an array detector is scanned over a code present in the form of a microfilm, with a reduction in the data to be recorded being achieved as a result of the specific type of encoding. A challenge in this method consists of recognizing moving parts and, in the process, of in particular capturing information in digital form.

German Patent No. DE 196 31 086 A1 has disclosed an active pixel image sensor row, which uses protective rings, protective diffusions or a combination of these two techniques in order to prevent electrodes generated at the edge of an active region from being incident on an image sensor matrix. U.S. Publication No. 2007/0046803 A1 has disclosed a CMOS image sensor with a plurality of active pixel rows and one optically black pixel row. The optically black pixel row is activated in order to generate a respective optically black signal when each of at least two of the active pixel rows are activated. Both documents relate to specific aspects of the chip design of optically sensitive chips.

However, known approaches for evaluating images of test elements have the problem that an image has to be detected with a comparatively high resolution and has to be analyzed, for example using pattern recognition methods. In this case, a comparatively high resolution for example means a total of 1 million pixels, with, however, pixel arrays with a smaller number of pixels also being used in principle. Nevertheless, it is still necessary to transmit a large amount of data to peripheral electronics within a short space of time, e.g. 100 ms, and to use the latter to evaluate said data online; this significantly restricts the service life of the battery, particularly in the case of portable, e.g. handheld, instruments due to the high clock rates of the electronics required for this and due to the large number of computational operations. A partial solution is offered by pre-processing the image information in peripheral electronics. Such methods and devices are described in, for example, European Patent No. EP 1 351 189 A1, U.S. Publication No. 2005/0013494 A1 or in U.S. Publication No.

2003/0123087 A1. Alternatively, pre-processing in part already lends itself directly to a CMOS sensor, as described in e.g. U.S. Pat. No. 6,515,702 B1.

A method of a histogram evaluation was proposed as an alternative to a conventional on-chip or off-chip pattern recognition which subdivides the image into wetted, i.e. glucose-information carrying, and unwetted regions for further analysis. This method is described in European Patent No. EP 1 843 148 A1. Here, a frequency distribution is established for the detected light intensities, with the frequency distribution having at least a first maximum caused by unwetted portions and a second maximum caused by wetted portions. The concentration of the analyte is established from the frequency distribution. However, even though the histogram analysis, which for example is implemented directly on the CMOS image sensor, would significantly reduce the amount of data to be transmitted and evaluated, the proposed method, if preceding image preprocessing is to be avoided, realistically would still require significantly more than 10 000 pixels in order thus to enable a sufficiently precise glucose measurement.

In addition to the analysis and proposals outlined above, there moreover is the requirement from the point of view of metrology that the dimensions of typical measuring instruments are to be kept very small, which leads to significant consequences in terms of the flexibility of the optical unit layout. With increasing miniaturization, the lens used to image a test spot on a detector must have an increasingly higher refractive index, leading to increasing aberrations. By way of example, this results in the imaging being out of focus at the edges. In order not to compromise the image quality any further, the smallest possible pixels are desirable from an optics point of view. At the same time, the pixel dimensions on the detector are, as a result of the semiconductor processing technology of such sensors, generally restricted to values of at least 4 µm, of preferably more than 8 µm and of particularly preferably more than 20 µm. This means that semiconductor technology in general requires pixels that are as large as possible, whereas the optical unit layout requires ones that are as small as possible. This conversely leads to the necessity of magnifying imaging and, as a result, to a further reduction in the imaging quality in practical, cost-effective systems. Furthermore, the requirements on the positional tolerance of the test field increase in conventional systems with an increasing magnification scale.

SUMMARY

This disclosure provides a device and a method which avoid the above-described disadvantages of known devices and methods. In particular, it should be possible to embody the device as a portable handheld instrument and said device should, while having simple electronics, a simple optical unit and low resource and energy consumption, be able to perform a reliable optical detection of at least one analyte in a bodily fluid with high measurement accuracy.

In a first aspect of this disclosure, a device is proposed for detecting at least one analyte in a bodily fluid, which device comprises at least one test element. By way of example, the device can be embodied as a portable instrument, more particularly as a handheld instrument or manual instrument, and can, for example, comprise an internal energy source, for example an electrical energy store such as e.g. a battery and/or a rechargeable battery. In particular, the device can be embodied as portable test instrument.

In principle, any types of detectable analytes and/or parameters of the bodily fluid can be considered as an analyte. It is typical for the analyte to comprise at least one metabolite. Examples of typical detectable analytes include glucose, cholesterol, lactate or other analytes. In principle, it is also possible to detect combinations of analytes. By way of example, blood, interstitial fluid, saliva, urine or other bodily fluids are used as bodily fluid.

The device comprises at least one test element. A test element should generally be understood to mean an element which is designed such that it carries out at least one detectable change as a result of the analyte, for example as a result of contact with the analyte. By way of example, the test element can, for this purpose, comprise at least one test chemical, which can carry out such analyte-specific detection. Examples of such detectable changes are optically detectable changes, for example changes in color or changes in grayscale values and/or other optically detectable changes. By way of example, the test element can have at least one test field which comprises the test chemical. Here, a test field should generally be understood to mean a planar element which comprises the at least one test chemical. However, the test field can additionally comprise a layered design, wherein at least one further layer, for example a separation layer, can be applied in addition to an at least one layer comprising the test chemical. Thus, the test field can for example comprise a sample application area which can for example be a surface of the test field. By way of example, a separation layer can be provided as the uppermost layer; it can separate out interfering constituents of the sample, e.g. red blood cells. The test field can furthermore comprise at least one detection layer, which in turn comprises the test chemical and which can preferably be provided below the optional separation layer. Furthermore, the test field can have a detection side, from which in this case the detectable change can be observed. By way of example, the detection side can be arranged opposite to the sample application side. By way of example, the layered design can be embodied such that the interfering constituents of the sample such as e.g. red blood cells are no longer visible from the detection side. By contrast, the change in the at least one property should be observable from the detection side.

The test element comprises at least one at least two-dimensional evaluation region. By way of example, this evaluation region can be arranged on the detection side of the test element, e.g. of the test field. By way of example, the evaluation region can be part of the detection side and can for example be arranged on a side of the test field lying opposite to the sample application side. In general, an evaluation region should be understood to mean a region of the test field which is influenced, in an optically identifiable manner, by the sample of the bodily fluid in the case of a test in the device running according to plan. By way of example, this can be the region within which an optically visible change occurs on the detection side when a capillary filled with the sample is pressed onto the sample application side, be it as a result of the sample itself or as a result of an analyte-specific reaction within a test chemical of the test element. Hence, the evaluation region is defined by a use of the device as intended as the part of the test element, more particularly as the part of a detection side of a test field, within which a change occurs during intended use, e.g. during an intended transfer of the sample onto the test field. Excluded therefrom are transfer processes which do not run correctly, e.g. transfer errors of the sample onto the test element, e.g. flooding of the test element and/or underdosing the sample. By way of example, the test element can generally comprise a sample application region, onto which sample is transferred in a spatially delimited fashion when the device is used as intended, wherein the sample application region can for example be arranged on a sample application side of the test field. The evaluation region can comprise a region lying opposite the sample application region, for example a projection of the sample application region from the sample application side onto the detection side of a test field. By way of example, the sample application region can have a substantially rectangular shape, corresponding to an outer form of a capillary. In this case, the evaluation region can, for example, also have a substantially rectangular design, as projection of the sample application region from the sample application side onto the detection side.

The device furthermore comprises at least one spatially resolved optical detector. By way of example, this detector can comprise at least one spatially resolved optical sensor, for example a sensor array with a plurality of sensor pixels, i.e. optical individual sensors. Furthermore, as will still be explained in more detail below, the detector can comprise an optical unit which is designed to image the evaluation region onto the optical sensor, e.g. a sensor chip. By way of example, this optical unit can comprise one or more lenses and/or other imaging optical systems.

The detector has a multiplicity of pixels, for example as components of an optical sensor, for example of a sensor chip. Here, pixels should generally be understood to mean image-sensitive individual sensors, which can for example be arranged in a matrix arrangement. In this case, the detector, for example an optical unit of the detector, is designed to image at least part of the test element onto an image region. Here, an image region can be understood to mean a portion of the sensor pixels of the detector, more particularly of the optical sensor of the detector, for example a spatially contiguous portion of sensor pixels of the sensor, on which the part of the test element is imaged such that these sensor pixels receive image information from the imaged part of the test element. By way of example, part of the detection side of the test element, for example of the test field, can be imaged onto the image region. In addition to the imaged part of the test element, the detector can furthermore be designed to image further parts of the device, for example part of a lancet and/or capillary, onto the optical sensor. Accordingly, provision can be made for further image regions, which do not contain images of the test element but rather images of other parts of the device.

When imaging either the entirety or at least part of the test element, for example when imaging the detection side of the test element or of the test field or of part of the detection side, onto the image region, at least part of the evaluation region should be imaged onto an evaluation image region. Hence the evaluation region can be, at least in part, a component of the part of the test element which is imaged onto the image region. The evaluation image region is a subset and/or portion and/or part of the image region, for example a contiguous portion of sensor pixels of the sensor, which receive image information of the evaluation region when the evaluation region is imaged.

Here, it is proposed that the detector is matched to the test element or, overall, to the device such that a predetermined minimum number of pixels are provided within the evaluation image region for each dimension of the evaluation image region. This means that in each direction of the evaluation image region, e.g. in an x- and a y-direction, a minimum number of pixels $N_x$ and $N_y$ are respectively provided. As will still be explained in more detail below, the evaluation image region can for example have a direction y perpendicular to a longitudinal extent of the capillary or of the print of the capillary or of the image of the capillary on the evaluation image region, which is also referred to as transverse dimension or transverse side, and a coordinate x parallel to a longitudinal extent of the capillary or of the image of the capillary or of the image of the print of the capillary, which can also be referred to as longitudinal direction or longitudinal side. In particular, the transverse side and the longitudinal side can be substantially perpendicular to one another. The pixels are arranged in a two-dimensional matrix arrangement. The matrix arrangement has pixel rows and pixel columns. The pixel rows are arranged substantially parallel to a longitudinal direction of the evaluation region and/or of the evaluation image region.

In particular, as illustrated above, the evaluation region can be part of the test element. In particular, this can be part of a test field of the test element with at least one detection chemical for detecting the analyte, for example part of a detection side of the test field. In particular, the device can be designed such that bodily fluid is transferred onto a sample application region of the test element, for example onto a sample application side of a test field, for detecting the analyte. By way of example, if the device is used as intended, this sample application region can be spatially delimited, for example by virtue of the latter substantially corresponding to a print of a capillary on the test field, for example on the sample application side, i.e. to a region within which bodily fluid, e.g. blood, is transferred onto the sample application side from the capillary.

In particular, the device can be designed such that bodily fluid, more particularly blood and/or interstitial fluid, is transferred onto the test element for detecting the analyte. As illustrated above, this transfer can be brought about on a spatially delimited sample application region of a sample application side of a test field. However, in principle, other embodiments are also possible. By way of example, the transfer can be brought about by virtue of causing a transfer element to approach the test element, for example at a sample application side of a test field. This approach can lead right up to physical contact between the transfer element and the sample application side of a test field. By way of example, the transfer element can, as illustrated above, comprise a capillary, for example a capillary within a lancet. Such lancets with capillaries are often also referred to as microsamplers. The sample application region can in particular correspond to the evaluation region, for example by virtue of the evaluation region being a region of the test element, within which, as described above, a change occurs which can be detected by optical means in the case of a correct transfer of bodily fluid onto the sample application region. By way of example, the evaluation region can be a region of a test field lying opposite the sample application region, for example a projection of the sample application region from the sample application side onto the detection side provided that e.g. lateral expansion effects when penetrating the test field can be discarded. By way of example, this is how it is possible to transfer the bodily fluid onto the sample application region on the sample application side of a test field, while detection takes place from the rear side, i.e. from the detection side, where an optically detectable change can be detected within the evaluation region.

As illustrated above, the device can in particular comprise at least one lancet element with at least one capillary. By way of example, the device can comprise a drive device, by means of which a puncturing movement of the lancet element can be driven, for example comprising a forward movement (piercing movement) and a return movement. Bodily fluid can be taken up in the capillary during the piercing procedure and/or during the return movement. The device can then, in particular, be designed to take up bodily fluid by means of the capillary and to transfer bodily fluid onto the test element, in particular onto a test field with at least one detection chemical, by causing the capillary to approach the test element. By way of example, this transfer can be onto a sample application region of a sample application side of the test element, in particular of the test field. In particular, the approach of the capillary to the test element, for example to the sample application side of the test field, can be brought about by means of at least one actuator. Thus, provision can for example be made for an actuator which causes the capillary at least partly filled with the bodily fluid to approach the test field, for example the sample application side, until the transfer takes place. By way of example, the capillary can be pressed onto the sample application side of the test field. However, in principle, a contact-free approach is also possible, for example an approach to within such a short distance that there is a sample transfer from the capillary to the sample application side by means of e.g. capillary forces between the lancet and the test field and/or adhesion forces. However, as an alternative to an actuator, or in addition thereto, the device can also have a different design for causing the capillary to approach the test element. By way of example, the lancet or the capillary can be guided during the retrieval movement of the lancet such that it describes a path in space within which approaching of the test element, for example the sample application side of the test field, takes place. By way of example, provision can be made for curved guidance of the lancet, within the scope of which the lancet describes a curved path by means of which the lancet or the capillary is pressed against and/or caused to approach the test field. Various other embodiments or combinations of the aforementioned and/or other embodiments for causing the capillary to approach the test element are possible.

As described above, the evaluation region can in particular be a region of the test element within which an optically detectable change occurs as a result of the transfer of the bodily fluid onto the test element. This change can be caused by the bodily fluid itself or, to a greater or lesser extent, by the at least one analyte contained in the bodily fluid and, for example, the reaction of said analyte with the at least one test chemical. As described above, the evaluation region can therefore in particular be part of a test field, for example part of a detection side of a test field, which can, for example, also lie opposite a sample application side of the test field, for example by virtue of the evaluation region corresponding to a projection of a sample application region of the sample application side when the device is used as intended. By way of example, the evaluation region can be a region in which an optically detectable change, for example a change in color and/or a change in grayscale value, occurs as a result of the sample. In particular, the evaluation region can be an image of the capillary from the sample application side onto the detection side, or a portion of this projection.

In particular, the capillary can have a width of 50 to 200 µm, more particularly of 90 to 150 µm and particularly preferably of approximately 120 µm. As an alternative, or in addition thereto, the capillary can, in particular, have a length of at least 1 mm, more particularly at least 2 mm and preferably a length of 2 to 4 mm. Capillaries typically have a depth of 20 to 150 µm, for example a depth of 50 to 120 µm. However, in principle, other dimensions of the capillary are also possible.

In particular, the device can be designed to recognize the evaluation region automatically. To this end, the device can for example have an evaluation device, which can for example be wholly or partly integrated into the detector but which can however also be wholly or partly arranged externally. By way of example, this evaluation device can comprise one or more data-processing devices. Alternatively, or in addition thereto, the evaluation device can however also have a simpler design and can for example comprise one or more comparators and/or other electronic devices in order to compare signals of the detector, for example signals of the optical sensor and/or of one or more pixels of the optical sensor, to one or more thresholds. As an alternative to the object of recognizing the evaluation region, or in addition thereto, the evaluation device can also have other objects, for example the objects of carrying out a data reduction, the object of recognizing work processes that are not as intended, the object of preprocessing image data or similar objects.

Various methods can be used for automatic recognition of the evaluation region. A first method variant makes use of the fact that the evaluation region can preferably constitute a projection of a capillary onto the detection side of the test element. Accordingly, a pattern recognition method, in which a lancet and/or a capillary of the device is recognized, can be used in this first method variant. Thus, the device can for example be designed such that the capillary protrudes beyond the test element, such that the detector records not only an image of the detection side of the test element but also a portion of the lancet and/or of the capillary in which the latter does not rest on the sample application side of the test element. By way of example, as illustrated above, provision can be made for a test field with a sample application side, which the lancet with the capillary is caused to approach, and with an opposing detection side which is observed by the detector. If the lancet with the capillary protrudes laterally beyond the test field, the detector preferably records part of the lancet and of the capillary, which part is not optically covered by the test field. In particular, the pattern recognition method can be designed such that an extrapolation of the lancet and/or capillary onto the test element is identified as an evaluation region. Examples of this first method variant will be explained in more detail below.

In a second variant of the method or the device, which can be used as an alternative or in addition to the variant above, use can be made of a signal-change method. In a signal-change method, changes in the signals of the optical sensor of the detector are monitored. Here, a region of the test element within which an optically detectable change occurs as a result of transferring the bodily fluid onto the test element is identified as an evaluation region. As illustrated above, this optically detectable change can be a change which is caused by the bodily fluid itself, for example by virtue of the bodily fluid itself leading to a darkening and/or a change in the grayscale value and/or a change in the color within the evaluation region on the detection side of the test element, for example of the test field. However, these optical changes can, alternatively or in addition thereto, also be caused by the analyte to be detected itself. In both cases, the position of the evaluation region can be determined by means of the signal-change method. By way of example, an evaluation region can be recognized and defined by recognizing inhomogeneities, caused by the capillary edge, in the optically detectable change, for example in a discoloring and/or darkening and/or change in a grayscale value.

This aspect of these teachings can also be implemented independently of the remaining aspects of this disclosure. Thus, in a coordinate aspect, a method is proposed for recognizing an evaluation region of a test element, in particular by using a device as described above or in the following text. However, in principle, the use of other types of devices is also feasible. In general, use is made within the method of at least one lancet element, for example as per the description above, with at least one capillary. Bodily fluid held in the capillary is transferred onto the test element, for example onto a sample application side of a test field of the test element. Furthermore, at least one spatially resolved optical detector, for example as per the description above, is used to image at least part of the test element, for example part of a detection side of a test field of the test element, onto an image region, for example an image region of an optical sensor of the detector. Here at least part of the evaluation region of the test element is imaged onto an evaluation image region. The method is carried out such that the evaluation region is recognized automatically, from a method selected from the following: a pattern recognition method, wherein, in the pattern recognition method, the lancet and/or the capillary is recognized, wherein an extrapolation of the lancet and/or of the capillary onto the test element is identified as evaluation region; and a signal-change method, wherein a region of the test element within which an optically detectable change occurs as a result of the transfer of the bodily fluid onto the test element is identified as evaluation region. By way of example, the latter method variant can be carried out by means of simple comparison methods, for example by monitoring one pixel, a plurality of pixels or all pixels of an optical sensor of the detector, comparing the signals from these pixels with signals recorded in advance and for example comparing the signal changes to thresholds. If the signal changes exceed predetermined thresholds, the conclusion can for example be drawn that wetting has taken place and that the associated pixels are arranged within the evaluation region or within the evaluation image region. In respect of further possible embodiments, reference can be made to the description above.

In particular, the detector can be designed such that it, or an optical sensor of said detector, has a total number of no more than 1000 pixels, preferably a total number of no more than 500 and particularly preferably a total number of no more than 256 pixels. By way of example, use can be made of detectors which have a longitudinal side and a transverse side. As defined above, the longitudinal side can in particular be defined as x-direction which in the normal case, i.e. if the device is used as intended, is arranged parallel to the capillary or parallel to the image of the capillary in the image region. Accordingly, the transverse side can be aligned perpendicular to the capillary or perpendicular to the image of the capillary and can for example be defined as y-direction. In particular, the detector can be designed such that the latter has at least 3 pixels, preferably no more than 100 pixels, more particularly 20 to 50 pixels and particularly preferably 32 pixels in the direction of the transverse side. Furthermore, in the direction of the longitudinal side, i.e. in the x-direction, the detector can have at least 1 pixel, preferably 2 to 20 pixels, more particularly 5 to 10 pixels and particularly preferably 7 pixels. However, in principle, other embodiments are also possible. It is particularly preferable for the detector to be embodied such that at least 3 pixels, more particularly 5 to 30 pixels and particularly preferably 10 pixels are arranged within the evaluation region, i.e. within the region in which optically detectable changes are noticeable if the device is used as intended and if, for example, bodily fluid is transferred onto the test element as intended.

In particular, as explained above, the evaluation region can have a longitudinal side and a transverse side, more particularly a longitudinal side aligned parallel to the capillary or to the image of the capillary on the image region and a transverse side aligned perpendicular to the capillary or the image thereof. As explained above, the transverse side can be defined as y-direction, and the longitudinal side can be defined as x-direction, with these directions preferably being substantially perpendicular to one another, for example with a deviation of no more than 5°. Pixels with the same y-coordinate can then be referred to as pixel row and pixels with the same x-coordinate can be referred to as pixel column. In particular, the detector can be designed such that at least 3 pixel rows, more particularly 3 to 10 pixel rows, are arranged within the evaluation region in the direction of the transverse side. Alternatively, or in addition thereto, the detector can be designed such that at least one pixel column, preferably at least three pixel columns, more particularly 3 to 10 pixel columns and particularly preferably 7 pixel columns are arranged in the direction of the longitudinal side.

In particular, the pixels can have an elongate pixel geometry. Here, an elongate pixel geometry should be understood to mean a geometry in which the pixels have a greater extent along one dimension than along another dimension. By way of example, the pixels can have a greater length in the x-direction than in the y-direction. By way of example, the evaluation region can thus have a longitudinal side and a transverse side, more particularly a longitudinal side aligned parallel to the capillary and a transverse side aligned perpendicular to the capillary. In particular, the pixels can have a length in the direction of the longitudinal direction, i.e. for example in the x-direction, and a width in the direction of the transverse side, preferably in the y-direction. Here, the length can preferably exceed the width. In particular, the length can exceed the width by at least a factor of 1.3, more particularly by at least a factor of 1.7 or at least a factor of 2 and particularly preferably by a factor of 2.3. In practice, such pixel geometries were found to be particularly suitable for elongate capillaries with typical dimensions, for example the capillary dimensions illustrated above, in order to reliably capture the evaluation region and evaluate the optically detectable changes. The length of the pixels can for example be 10 to 300 μm, preferably 50 to 100 μm and particularly preferably 70 μm. The width can for example be 5 to 200 μm, preferably 10 to 100 μm and particularly preferably 30 μm.

The pixels are be arranged in a two dimensional matrix arrangement. The matrix arrangement has pixel rows and pixel columns, for example as described above. Thus, the rows can for example be aligned parallel to the x-direction, and the pixel columns can be aligned parallel to the y-direction. The pixel rows are arranged substantially parallel to the longitudinal direction of the evaluation region, for example substantially parallel to an image of an axis of longitudinal extent of the capillary or of the image of the capillary in the image region. Here, "substantially parallel" can more particularly be understood to mean a deviation from being completely parallel of less than 5°, more particularly a deviation of less than 2° and particularly preferably a deviation of 1° or less, more particularly 0°. The longitudinal direction of the evaluation region, i.e., for example, an axis of longitudinal extent of the capillary and/or of an image of the capillary in the image region, can thus be arranged substantially parallel to the pixel rows. This embodiment of the device, particularly in combination with the above-described elongate pixels, leads to a particularly efficient evaluation of the evaluation region in the case of the smallest possible number of pixels, the option of using large pixel areas and nevertheless having reliable evaluation of a multiplicity of pixels within the evaluation region.

In particular, the detector can, as already explained above, have a spatially resolving optical unit. This spatially resolving optical unit can for example have one or more lenses and/or other optical imaging systems. Furthermore, the spatially resolving optical unit can have further optical elements with non-imaging properties, for example stops or the like. Furthermore, provision can be made for filters, mirrors, other types of optical deflection elements or other optical elements.

The spatially resolving optical unit can in particular be designed to image the evaluation region on the evaluation image region with a magnification of 3:1 to 0.5:1, preferably with a magnification of 2:1 to 0.8:1, particularly preferably with a magnification of 1.1:1 to 0.9:1 and ideally of 1:1. Here, a magnification of 3:1 means that the evaluation image region is larger than the evaluation region by a factor of 3. Thus, the optical unit is ideally designed such that it does not have any magnification in the actual sense of the word, but rather that the dimensions of the evaluation image region substantially correspond to the dimensions of the evaluation region.

As described above, determining the evaluation region is based on proper wetting. By way of example, the evaluation region can comprise a print of the capillary or a projection of the capillary onto the detection side. Apart from proper wetting, during which, apart from inhomogeneities in the edge region of the capillary which generally cannot be avoided, bodily fluid is merely transferred from the capillary onto the test element, for example onto the sample application side, various transfer errors and/or wetting errors may occur. Thus, for example, the capillary may be filled to an insufficient extent such that too small an amount of bodily fluid is transferred onto the sample application side. However, this case of incomplete filling and/or incomplete transfer of bodily fluid onto the test element only constitutes one of a number of error cases. By way of example, this case can occur if an unsuitable puncturing point into body tissue was chosen such that, for example, a too small amount of bodily fluid was taken up by the microsampler during a puncturing process and/or sample taking process. The opposite case can also occur. By way of example, in this case, the whole lancet can be wetted by bodily fluid or blood, which is then transferred onto the test element such that, for example, the test element is flooded by bodily fluid. This case can also lead to errors, for example by virtue of, as will still be explained in more detail below, no non-wetted regions being available within the image region, i.e. regions outside of the evaluation region which could serve as reference value and/or "blank value" for characterizing the discoloring or the optical change in the test element.

Therefore it is particularly preferable for the device to be designed to characterize, more particularly to evaluate, a wetting of the test element with the bodily fluid. By way of example, this characterization can be brought about by virtue of the fact that an evaluation device is provided, which evaluates signals of the optical sensor of the detector, for example an evaluation device with the above-described features. By way of example, the evaluation device can characterize the wetting such that proper wetting, i.e. a proper transfer of bodily fluid onto the test element, is distinguished from one or more error cases. By way of example, a proper, successful transfer of bodily fluid onto the test element can be distinguished from a case of flooding, in which bodily fluid is even transferred from outside of the limits of the capillary onto the sample application side of the test element, and a case of an underdose, in which there is incomplete wetting of the sample application side with bodily fluid even within the actual evaluation region. In particular, the characterization can be undertaken such that the device is designed to compare a plurality of pixels to one another in at least one dimension. By way of example, it is possible to compare neighboring pixels to one another in at least one direction, for example in a direction parallel to a longitudinal side of the evaluation region. In particular, there can be a comparison of two or more neighboring pixels in a pixel row aligned parallel to the evaluation region. In particular, the signals of the pixels within the evaluation region can be compared in order to recognize whether pixels which actually should indicate wetting in actual fact exhibit such wetting. By way of example, this is a way of recognizing an underdose, for example as a result of incomplete filling of the capillary and/or an incomplete transfer of the bodily fluid onto the test element. On the other hand, it is possible to recognize if pixels which should not in actual fact indicate wetting, i.e. pixels situated outside of the evaluation region, do in fact detect wetting, as a result of which it is possible for example to recognize flooding and/or an overdose. By way of example, the characterization can be brought about such that there is a comparison of neighboring pixels from one pixel row, which is substantially arranged parallel to the longitudinal direction of the evaluation region, with, for example, it being possible to make use of a thresholding method. By way of example, this is how the difference in the signals of neighboring pixels can be formed and compared to at least one threshold. If the difference exceeds the at least one threshold, it is possible to deduce the presence of, for example, underwetting and/or an underdose and/or another error. Here, the longitudinal direction of the evaluation region is preferably substantially aligned parallel to the edges of the capillary and/or of the capillary channel of the capillary. As explained above, the capillary is preferably caused to approach the test element, for example pressed onto the latter, in order to transfer the bodily fluid. As a result of a comparison of the neighboring pixel of the pixel row aligned parallel thereto, it is therefore possible to recognize an incorrectly filled capillary and/or an incorrect bodily fluid transfer, for example as a result of incomplete and/or fragmentary filling of the capillary.

As illustrated above, the detector can in particular be embodied as a compact detector. Thus, the detector can in particular have a detector assembly, more particularly a detector chip, wherein, for example, the evaluation device can be wholly or partly integrated into the detector assembly, more particularly the detector chip. The evaluation device can be designed to carry out a whole or partial image evaluation of the image region and/or of the evaluation image region. In particular, the detector chip can be embodied as an application-specific integrated circuit (ASIC).

In particular, the device can be designed to recognize a blank value. Here, a blank value characterizes an optical property of the image region and/or of the evaluation image region without wetting the test element with bodily fluid. In particular, the recognition of the blank value can in turn take place using an evaluation device, which can be wholly or partly integrated into the detector. In particular, the device can be designed to determine the blank value according to one or more of the methods described below.

In a first variant of a method which the device, more particularly the evaluation device, can be designed to carry out, it is possible to record a temporal image sequence. Here, a temporal image sequence should be understood to mean a multiplicity of items of image information from the optical sensor, which were recorded at different, successive times, for example images recorded at an interval of 100 ms. The evaluation region can be determined from this temporal image sequence, for example by means of one or more of the above-described methods. Here it is possible to recognize at least one pixel, preferably a number of pixels, arranged within the evaluation region, and it is possible to determine at least one initial value of the pixel from the temporal image sequence and use said initial value as blank value. In other words, it is possible initially to establish the evaluation region from the temporal image sequence and then to determine one or more initial values for one or more pixels within the evaluation region from the recorded image sequence, which initial values can then serve as blank value; this corresponds to "rewinding" the film of the image sequence. An advantage of this method lies in the fact that it is possible to determine a blank value for each pixel to be evaluated, which blank value precisely corresponds to this pixel.

Alternatively, or in addition thereto, it is possible to use a method in which an initial value of all pixels in the image region is stored, or at least an initial value of a plurality of pixels in the image region. It is then possible to establish the evaluation region from a temporal image sequence of the pixels. Pixels outside of the evaluation image region can be discarded, and so there can be data reduction in this manner. At least one initial value of a pixel within the evaluation image region can then be used as a blank value. An advantage offered by this method variant lies in significant data reduction because it is possible to discard pixels outside of the evaluation image region during the recording of the temporal image sequence as soon as it is clear where the evaluation image region is positioned within the image region, and so there is no longer the need to store image sequences of the whole image region, but only image sequences of the pixels of the evaluation region.

In a third method, which can in turn be used as an alternative or in addition to the above, it is possible to establish the evaluation region, for example by means of one or more of the above-described methods. As a blank value, it is then possible to use at least one pixel outside of the evaluation image region, i.e. a pixel on which a region of the test element is imaged that is situated outside of the evaluation image region, as a blank value. An advantage offered by this method variant is that merely a small amount of data needs to be stored. By way of example, the blank value can be determined solely on the basis of an image after the reaction of the analyte, without there being a need for storing a history or a temporal image sequence. However, in principle, it is also possible to use other methods for establishing one or more blank values. Compared to known devices and methods, the proposed device and the proposed method have a multiplicity of advantages. Thus, in particular, this disclosure offers an advantageous alternative to the use of conventional image sensors with more than 10 000 pixels, as can for example be used for the histogram analysis according to EP 1 843 148 A1. In particular, these teachings are based on the insight that, on the one hand, a spatial resolution preferably with at least approximately 10 pixels per capillary width, converted to the image of the capillary on the image region, is sought after. However, on the other hand, these teachings are based on the insight that the optical imaging quality is badly affected by lack of space in small, highly integrated and cost-sensitive instruments, in particular portable instruments. At the same time, these teachings acknowledge the fact that, from a semiconductor technology point of view, pixels that are as large as possible are expedient because optical sensors with pixels that are as large as possible, for example pixels with the above-described pixel geometry and/or pixel dimensions, enable a comparatively high fill factor of the optical sensors.

Thus, according to this disclosure, it is possible, in particular, to use an optical unit with 1:1 imaging. In the process, by using the above-described device in one or more of the above-described variants, it is possible, in particular, to increase the area per pixel and accordingly reduce the number of pixels. Reducing the amount of data and the data-analysis complexity accompanies a reduction in the number of pixels, for example to the above-described pixel numbers of the optical sensor, and so it is possible to achieve an improvement in all of the above-described critical boundary conditions of the device. At the same time, it is possible to match the pixel geometry to the detection method and the implementation, for example by a rectangular design of the pixels, wherein the pixel geometry can in particular be matched specifically to the geometry of the evaluation region, for example of the measurement spot, e.g. as a result of the capillary geometry.

In conclusion, the following embodiments are considered to be particularly advantageous within the scope of this disclosure:

EMBODIMENT 1

A device for detecting at least one analyte in a bodily fluid, comprising at least one test element with at least one two-dimensional evaluation region, furthermore comprising at least one spatially resolving optical detector having a plurality of pixels, wherein the detector is designed to image at least part of the test element onto an image region, wherein at least part of the evaluation region is imaged onto an evaluation image region, wherein the detector is matched to the test element such that a predetermined minimum number of pixels is provided for each dimension within the evaluation image region, wherein the pixels are arranged in a two-dimensional matrix arrangement, wherein the matrix arrangement has pixel rows and pixel columns, wherein the pixel rows are arranged substantially parallel to a longitudinal direction of the evaluation region and/or of the evaluation image region.

EMBODIMENT 2

The device according to the preceding embodiment, wherein the evaluation region is part of the test element, wherein the device is embodied such that bodily fluid is transferred onto the test element for detecting the analyte.

EMBODIMENT 3

The device according to one of the preceding embodiments, wherein the device comprises at least one lancet element with at least one capillary.

EMBODIMENT 4

The device according to the preceding embodiment, wherein the device is designed to take up bodily fluid by means of the capillary, wherein the device is furthermore designed to transfer bodily fluid onto the test element by causing the capillary to approach the test element.

EMBODIMENT 5

The device according to the preceding embodiment, wherein the evaluation region is a region of the test element, in which an optically detectable change occurs as a result of transferring the bodily fluid onto the test element.

EMBODIMENT 6

The device according to one of the three preceding embodiments, wherein the capillary has one or more of the following dimensions:
  a width of 50-200 µm, more particularly of 90-150 µm and particularly preferably of 120 µm;
  a length of at least 1 mm, more particularly of at least 2 mm and preferably a length of 2-4 mm.

EMBODIMENT 7

The device according to one of the preceding embodiments, wherein the device is designed to recognize the evaluation region automatically.

EMBODIMENT 8

The device according to the preceding embodiment, wherein the device is designed to recognize the evaluation region according to method selected from the group consisting of:
- a pattern recognition method, wherein the device comprises at least one lancet element and/or at least one capillary, wherein, in the pattern recognition method, the lancet element and/or the capillary of the device are recognized, wherein an extrapolation of the lancet element and/or of the capillary onto the test element is identified as evaluation region; and
- a signal-change method, wherein a region of the test element within which an optically detectable change occurs as a result of a transfer of the bodily fluid onto the test element is identified as evaluation region.

EMBODIMENT 9

The device according to one of the preceding embodiments, wherein the detector has a total number of no more than 1000 pixels, preferably a total number of no more than 500 and particularly preferably a total number of no more than 256 pixels.

EMBODIMENT 10

The device according to one of the preceding embodiments, wherein the detector has a longitudinal side and a transverse side, more particularly a longitudinal side aligned parallel to a capillary of the device and a transverse side arranged perpendicular to the capillary, wherein the detector has at least 3 pixel rows, preferably no more than 100 pixel rows, more particularly 20-50 pixel rows in the direction of the transverse side, wherein the detector furthermore has at least 1 pixel column, preferably 2-20 pixel columns, more particularly 5-10 pixel columns and particularly preferably 7 pixel columns in the direction of the longitudinal side.

EMBODIMENT 11

The device according to one of the preceding embodiments, wherein at least 3 pixels, more particularly 5-30 pixels and particularly preferably 10 pixels are arranged in the evaluation region.

EMBODIMENT 12

The device according to one of the preceding embodiments, wherein the evaluation region has a longitudinal side and a transverse side, more particularly a longitudinal side aligned parallel to a capillary of the device and a transverse side arranged perpendicular to the capillary, wherein the detector is designed such that at least 3 pixel rows, more particularly 3-10 pixel rows are arranged in the direction of the transverse side within the evaluation region, and wherein the detector is furthermore designed such that at least 1 pixel column, preferably at least 3 pixel columns, more particularly 3-10 pixel columns and particularly preferably 7 pixel columns are arranged in the direction of the longitudinal side.

EMBODIMENT 13

The device according to one of the preceding embodiments, wherein the pixels have an elongate pixel geometry, wherein the evaluation region has a longitudinal side and a transverse side, more particularly a longitudinal side aligned parallel to a capillary of the device and a transverse side arranged perpendicular to the capillary, wherein the pixels have a length in the direction of the longitudinal direction and wherein the pixels have a width in the direction of the transverse side, wherein the length exceeds the width, preferably by at least a factor of 1.3, more particularly by at least a factor of 1.7 or at least a factor of 2 and particularly preferably by a factor of 2.3.

EMBODIMENT 14

The device according to one of the preceding embodiments, wherein the detector has a spatially resolving optical unit, wherein the spatially resolving optical unit is designed to image the evaluation region onto the evaluation image region with a magnification of 3:1 to 0.5:1, preferably with a magnification of 2:1 to 0.8:1, particularly preferably with a magnification of 1.1:1 to 0.9:1 and ideally of 1:1.

EMBODIMENT 15

The device according to one of the preceding embodiments, wherein the device is designed to characterize, more particularly evaluate, a wetting of the test element with the bodily fluid, wherein the device is designed to carry out the characterization by comparing a plurality of pixels in at least one dimension, preferably by comparing adjacent pixels of a pixel row aligned parallel to the evaluation region.

EMBODIMENT 16

The device according to one of the preceding embodiments, wherein the device is designed to recognize a blank value, wherein the blank value is an optical property of the image region and/or of the evaluation image region without wetting of the test element with bodily fluid, wherein the device is designed to determine the blank value according to a method, selected from the group consisting of the following methods:
- recording a temporal image sequence, wherein the evaluation region is determined, wherein at least one pixel arranged within the evaluation region is recognized and an initial value of the pixel is determined from the temporal image sequence and used as blank value;
- an initial value of the pixels of the image region is stored, the evaluation region is established from a temporal image sequence of the pixels, pixels outside of the evaluation region are discarded and at least one initial value of a pixel within the evaluation region is used as blank value; and
- the evaluation region is established, at least one pixel from outside of the evaluation region is used as blank value.

EMBODIMENT 17

A method for recognizing an evaluation region of a test element for detecting at least one analyte in a bodily fluid, in particular by using a device according to one of the preceding embodiments, wherein use is made of at least one lancet element with at least one capillary, wherein bodily fluid taken up into the capillary is transferred onto the test element, wherein at least one spatially resolved optical detector is used to image at least part of the test element onto an image region, wherein at least part of the evaluation region of the test element is imaged onto an evaluation image region, wherein the evaluation region is automatically recognized according to a method selected from the group consisting of:
- a pattern recognition method, wherein, in the pattern recognition method, the lancet element (114) and/or the capillary (116) are recognized, wherein an extrapolation of the lancet element (114) and/or of the capillary (116) onto the test element (120) is identified as evaluation region (136); and
- a signal-change method, wherein a region of the test element (120) within which an optically detectable change occurs as a result of the transfer of the bodily fluid onto the test element (120) is identified as evaluation region (136).

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

Figure 1:
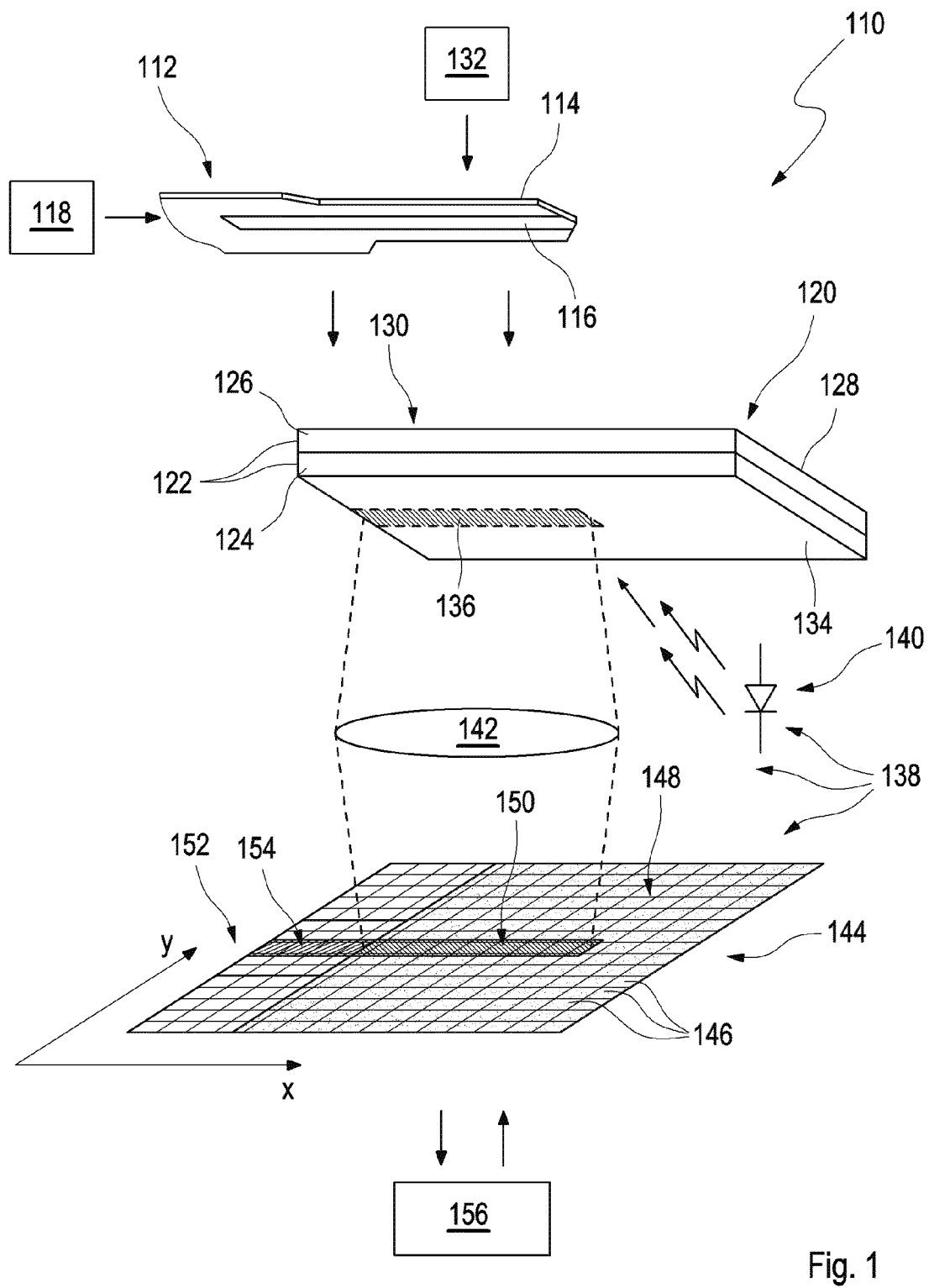
FIG. 1 shows an exemplary embodiment of a device according to this disclosure.

In a highly schematic exploded illustration, FIG. 1 illustrates a device 110 according to this disclosure for detecting at least one analyte in a bodily fluid. In the illustrated exemplary embodiment, the device 110 comprises a microsampler 112 with a lancet element 114 and a capillary 116. By way of example, this can be a metallic lancet, into which the capillary 116 has been inset as capillary gap. By way of example, the lancet element 114 can be driven to make a puncturing movement, for example by a drive device 118, for example one or more actuators (for example spring-driven actuators), with, for example, a piercing into the skin of a user taking place during a forward movement and a collection of bodily fluid in the capillary 116 taking place during a return movement.

The device 110 furthermore comprises at least one test element 120 in the illustrated exemplary embodiment. In particular, this test element 120 can comprise at least one test field 122, for example a test field 122 of a test strip and/or of a test tape with a plurality of test fields 122 and/or of a test disk with a plurality of test fields 122. In principle, other embodiments are also possible. By way of example, provision can be made for a plurality of microsamplers, with respectively one test field 122 being associated with each of them. By way of example, a microsampler 112 and at least one test field 122 can respectively be held in a chamber and together form a test. Other embodiments are also possible.

By way of example, the test field 122 can comprise a detection layer 124 with at least one test chemical which, when the at least one analyte to be detected is present, carries out an optically detectable and preferably analyte-specific reaction and/or experiences a detectable change. In respect of conventional test chemicals, reference can for example be made to the prior art described above. The test field 122 can furthermore comprise additional layers, for example one or more separation layers 126, which separate unwanted constituents of the sample of the bodily fluid, for example red blood cells which interfere with an optical detection, before the sample reaches the detection layer 124. Furthermore, the separation layer 126 can have reflective properties, for example by virtue of this comprising one or more reflecting substances, for example white pigments.

The test element 120 has a sample application side 128, on which, within a sample application region 130, at least part of the sample of the bodily fluid held in the capillary 116 is transferred onto the test field 122. To this end, the device 110 can comprise an approach device 132, which is designed to cause the capillary 116 to approach the sample application region 130 of the test field 122 after the sample is taken up into the capillary 116. By way of example, the approach device 132 can comprise one or more actuators, which actively cause the lancet element 114 to approach the test field 122, for example press it onto the latter. However, alternatively, or in addition thereto, the approach device 132 can also interact with the drive device 118, for example by virtue of the capillary 116 being caused to approach the test field 122 by a corresponding guide of the lancet element 114 when the lancet element 114 is withdrawn after a sample application movement. However, it is particularly preferable for the approach device 132 to have at least one actuator, for example a plunger, which presses the lancet element 114 onto the test field 122 such that a defined sample application region 130 is created, which is wetted by the sample in a defined manner.

A detection side 134 is provided on the side of the test element 120 opposite the sample application side 128. After the sample is transferred from the capillary 116 onto the sample application region 130 of the sample application side 128, an evaluation region 136 is formed on this detection side 134. By way of example, this evaluation region 136 can be a projection of the sample application region 130 in the case of a proper transfer of bodily fluid from the capillary 116 onto the sample application side 128. The evaluation region 136 can therefore in particular characterize the region of the detection side 134 within which an optically detectable change occurs after a proper transfer of the sample from the capillary 116 onto the test field 122.

In the illustrated exemplary embodiment, the device 110 furthermore comprises at least one detector 138, which, in the illustrated exemplary embodiment, is made up of a number of parts, but it can also be combined to form a common part, for example a detector assembly. The detector 138 for example comprises at least one light source 140 for illuminating the detection side 134, which light source can for example comprise a light-emitting diode. The detector 138 moreover comprises an optical unit 142, which is illustrated in a greatly simplified form in FIG. 1 and which, for example, can have one or more lenses. In the illustrated exemplary embodiment, the detector 138 furthermore comprises an optical sensor 144, for example a CCD chip and/or CMOS chip, which comprises a plurality of pixels 146 in a matrix arrangement. The pixels 146 preferably have a rectangular design and, with their longitudinal side, are aligned parallel to a longitudinal extent of the capillary 116 or the evaluation region 136 along an x-direction and, with their narrower transverse side, are aligned perpendicular to this direction of longitudinal extent in a y-direction. The optical unit 142 is designed to image part of the test element 120, more particularly part of the detection side 134 of the test element 120, on the optical sensor 144. It is additionally possible for further parts of the device 110 to be imaged. Thus, for example, it is possible past the edge of the test field 122 to image onto the optical sensor 144 part of the microsampler 112, preferably together with part of the capillary 116, by means of the detector 138 or by means of the optical unit 142 such that it is preferably possible for part of the capillary 116 to be observed directly. This is how a plurality of regions are preferably created on the optical sensor 144. This is how an image region 148, illustrated by dots in FIG. 1, is formed, on which the test element 120 and/or part of this test element 120, for example part of the detection side 134 of the test field 122, is imaged. Within this image region 148, the evaluation region 136 is imaged on an evaluation image region 150, which is illustrated in shaded fashion in FIG. 1. Furthermore, a region is optionally formed on the optical sensor 144, on which no constituents of the test element 120 are imaged. By way of example, an image 152 of the lancet element 114 can be created in this region, with an image 154 of the capillary 116, which image was recorded past the edge of the test field 120. The evaluation image region 150 thus substantially constitutes a continuation of this image 154 of the capillary 116, as illustrated symbolically in FIG. 1.

The device 110, more particularly the detector 138, can furthermore comprise at least one evaluation device 156, which is indicated symbolically in FIG. 1. The latter can also be wholly or partly integrated into the detector 138, for example into a detector assembly. By way of example, as illustrated above, the evaluation device 156 can comprise at least one data processing device, for example at least one microcontroller, and/or other electronic components such as e.g. logic components and/or memory components. By way of example, the evaluation device can, together with other components of the device 110, be designed to carry out a method according to this disclosure. The evaluation device 156 can for example carry out an image evaluation.

Figure 3:
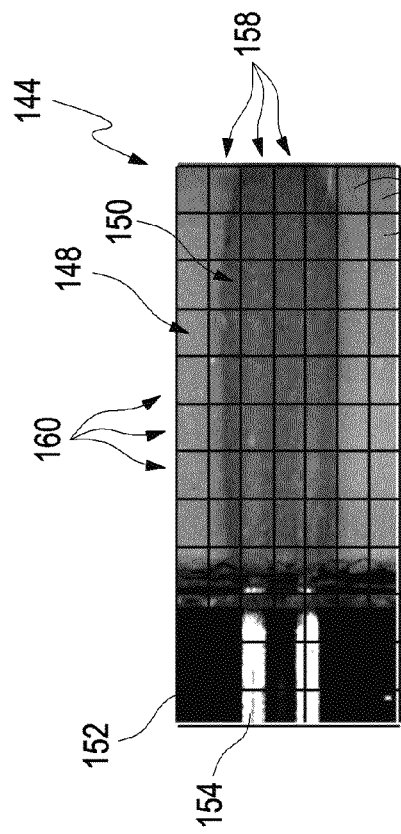
FIGS. 2A and 3A contrast a conventional image of an evaluation region (FIG. 2A) and an image according to this disclosure (FIG. 3A)
FIGS. 2B and 3B show a comparison between a conventional device (FIG. 2B) and a device according to this disclosure (FIG. 3B), in a perspective illustration.
Figure 3:
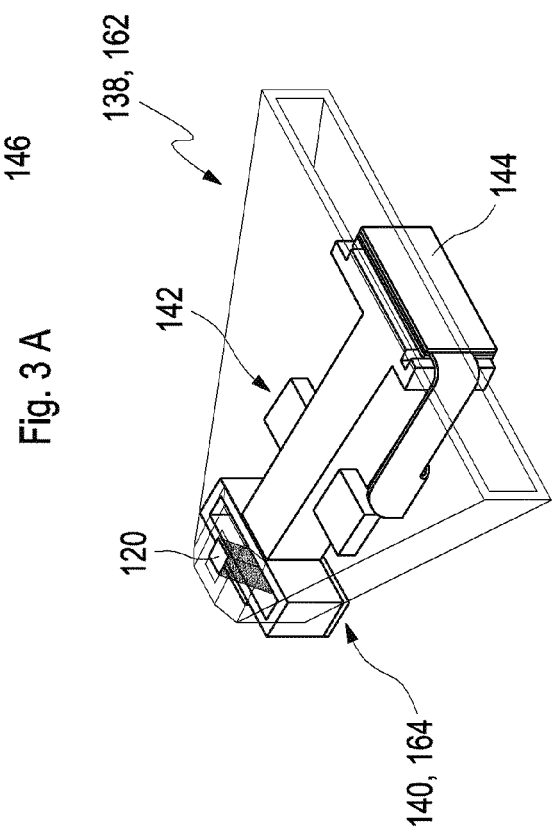
Figure 2:
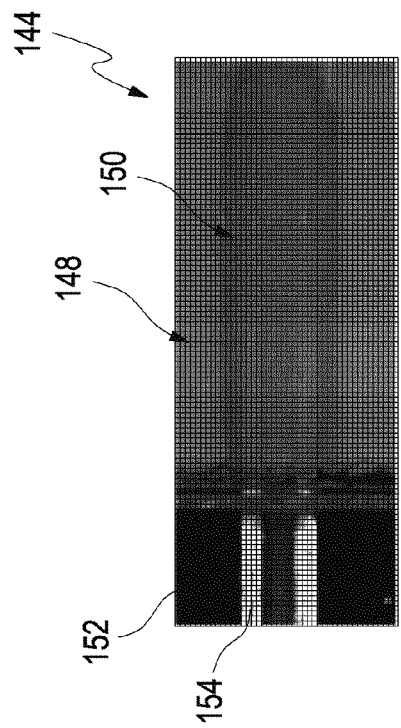
Figure 2:
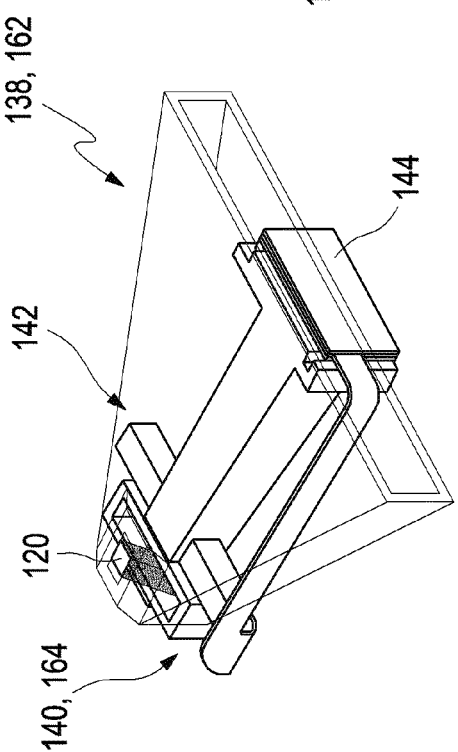

As illustrated above, an essential idea of this disclosure consists of using as detector 138 a detector with macro-pixels 146, i.e. large pixels, compared to conventional CMOS camera sensors. This is illustrated in FIGS. 2A and 2B, which show images on such optical sensors 144 in an exemplary fashion. Here, FIG. 2A shows a conventional CMOS chip, whereas FIG. 3A shows an optical sensor 144 with "macro-pixels" 146, which are particularly preferred within the scope of this disclosure. While there conventionally is a histogram evaluation in the case of the CMOS sensor 144 as per FIG. 2A, as described in e.g. EP 1 843 148 A1, an almost conventional evaluation can take place in the case of the detector 138 with the macro-pixels 146 as per the device 110 according to this disclosure, in which conventional evaluation for example the signals of each individual pixel 146 are stored and/or analyzed, for example with the aid of the evaluation device 156.

TABLE 1

Comparison of the properties of a conventional camera detection with histogram analysis and 3:1 imaging (central column) and a macro-pixel detection with 1:1 imaging (right-hand column).

|  | Camera | Macro-pixel |
| --- | --- | --- |
| Imaging | | |
| Magnification | 3:1 | 1:1 |
| Tolerances | + | + |
| Producibility | + | + |
| Volume for optical unit and optoelectronics | 2.57 cm$^3$ | 1.77 cm$^3$ |
| Optical sensor | | |
| Number of pixels | ~65 000 | ≤256 |
| Number of pixels with glucose information | ~2500 | ~10 |
| Pixel dimensions | 20 × 20 μm$^2$ | 30 × 70 μm$^2$ |
| Data transfer und Data analysis | | |
| Pre-analysis on the sensor chip | Required | If desired |
| Memory requirements per cycle (i.e. per 10 ms . . . 100 ms) | 256 × 2 byte | 256 × 2 byte |
| Analysis method | Histogram analysis | Special (simple) algorithm |

Table 1 compares conventional methods (column: "Camera") to analysis methods using a device 110 according to this disclosure with macro-pixels. Here, optical units were used in the conventional method, having a magnification of 3:1 as is typically required for imaging using CMOS chips. There is a total of approximately 65 000 pixels, of which approximately 2500 pixels in fact carry information in respect of the analyte (referred to as glucose information in this case), i.e. are pixels within the evaluation image region 150. The pixel dimensions are typically 20×20 μm$^2$ and these are square pixels. In the case of such methods, a pre-analysis of the data is typically necessary on the sensor chip itself because otherwise it is not possible to ensure the high image recording rates. This usually results in an amount of data per cycle of 256×2 bytes in the case of an image recording every 10 ms to 100 ms. By way of example, a histogram analysis can be used as analysis method.

By contrast, in the device 110 according to this disclosure, which uses macro-pixels 146, there was imaging with a magnification scale of 1:1 using the optical unit 142 in the illustrated series of tests. While the volume for the optical unit and the optoelectronics, i.e. the whole detector assembly, was approximately 2.57 cm$^3$ in the conventional devices, the volume for the optical unit and optoelectronics could, according to this disclosure, be reduced to 1.77 cm$^3$ in the device 110. The number of pixels was no more than 256. Of these, approximately 10 pixels carried glucose information. In the illustrated exemplary embodiment, the macro-pixels 146 had pixel dimensions of 30×70 μm$^2$ and a rectangular shape. There was no need for pre-analysis, e.g. pre-processing, of data on the sensor chip, although it can in principle be carried out if so desired. The memory requirements per cycle do not change in principle, even without pre-processing of the data. In the case of such small amounts of data as a result of the small number of macro-pixels, it is possible to use a special, simplified algorithm in order to determine the concentration of the analyte in the bodily fluid. By way of example, this algorithm can contain an evaluation of all pixels 146 arranged within the evaluation image region 150 or merely of central pixels.

By way of example, the evaluation image region 150 within the image region 148 can be recognized at first for this purpose, for example by means of one of the above-described methods. Thus, for example, it is possible to recognize a discoloring and/or a grayscale value change in the macro-pixels 146, as a result of which the evaluation image region 150 is defined. Subsequently, one or more macro-pixels 146, preferably situated centrally within the evaluation image region 150, can be used to read out the image information therefrom. By way of example, it is possible to recognize the evaluation image region 150 as a result of a change of grayscale values and/or as a result of recognizing the image 154 of the capillary, the continuation and/or extrapolation of which into the image region 148 constituting the evaluation image region 150. By way of example, the pixels 146 can be arranged in pixel rows 158 parallel to the x-direction, and hence parallel to the capillary 116, and in pixel columns 160 in the y-direction. The pixel row 158 situated furthest in the center of the evaluation image region 150 can for example be used for the evaluation. Alternatively, it is also possible to use a plurality of pixel rows 158 and/or parts of these pixel rows.

FIGS. 2B and 3B contrast detector assemblies 162 of conventional devices (FIG. 2B) and of devices according to this disclosure (FIG. 3B). Here, the reference sign 120 once again denotes a test element, for example a test field. By way of example, the test element 120 can be arranged in movable fashion relative to the detector assembly 162, for example as part of an analysis tape. Arranged below the test element 120 in the illustrated exemplary embodiment there is a light source 140 (not resolved in any more detail in the figures) and, optionally, a deflection device 164, which guides reflected light to optical sensors 144, to a CMOS chip with typically more than 10 000 pixels in the case of FIG. 2B and to an optical sensor 144 with macro-pixels 146, preferably with no more than 256 macro-pixels in the case of the FIG. 3B according to this disclosure. In the beam path, provision is furthermore made for an optical unit 142; to be precise, for an optical unit with a magnification of 3:1 and accordingly a greater installation space in the exemplary embodiment as per FIG. 2B and for an optical unit with preferably a magnification of 1:1 in the case of FIG. 3B according to this disclosure. It emerges clearly from FIGS. 2B and 3B that the installation space requirements of the embodiment according to this disclosure in FIG. 3B are significantly smaller than the installation space requirements as per FIG. 2B.

Figure 4:
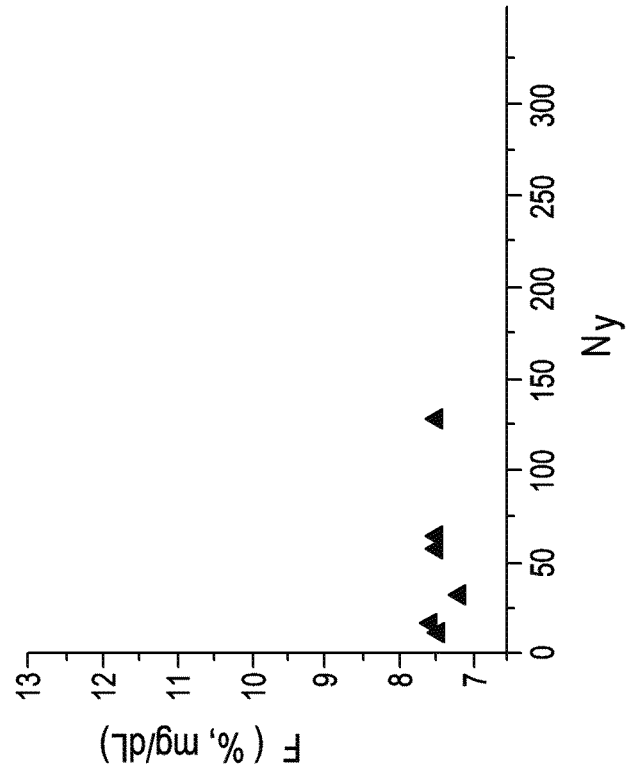
FIGS. 4 to 7 show measurement errors in various dimensions when using conventional detectors (FIGS. 4 and 6) compared to detectors according to this disclosure (FIGS. 5 and 7)
Figure 5:
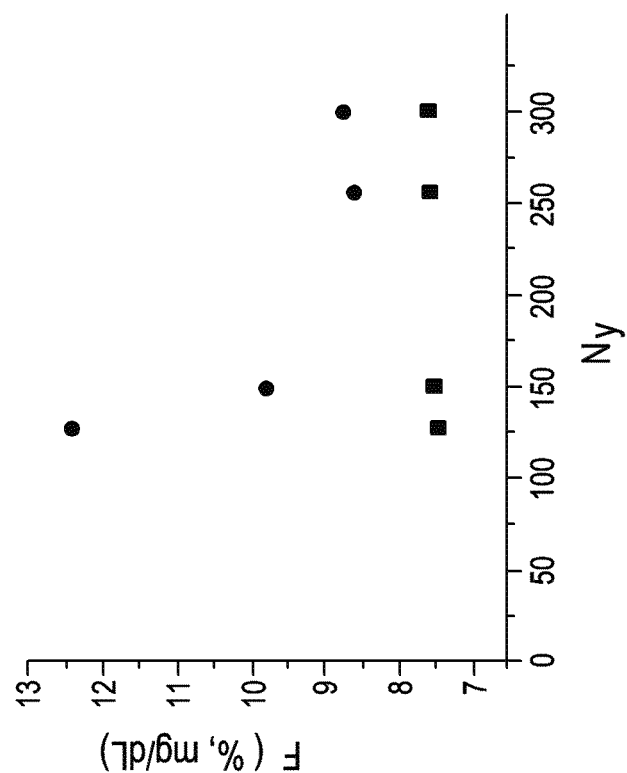
Figure 7:
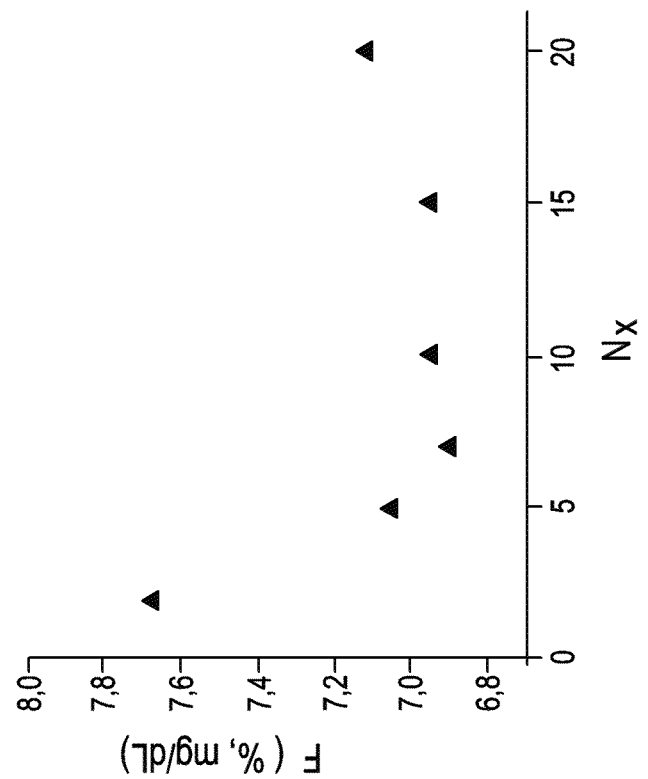
Figure 6:
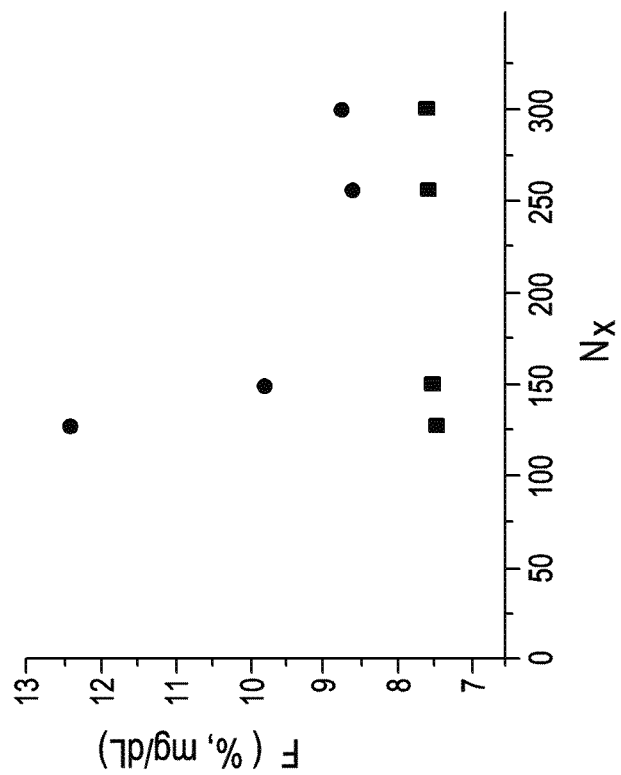

FIGS. 4 to 7 contrast comparison trials between conventional CMOS chips as per FIG. 2A and optical sensors 144 with macro-pixels 146, for example as per FIG. 3A. Plotted in each case on the vertical axis, which is respectively denoted by F, is an overall error of a glucose-concentration determination in percent. Plotted on the horizontal axis are a number of pixels of the optical sensor 144. Here $N_y$ denotes the number of pixels perpendicular to the capillary 116 or the image thereof (FIGS. 4 and 5), i.e. the number of pixel rows 158 on the optical sensor 144, and $N_x$ denotes the number of pixels 146 parallel to the capillary 116 or the image thereof (FIGS. 6 and 7), i.e. the number of pixel columns 160 per optical sensor 144. Here, FIGS. 4 and 6 show experiments with conventional CMOS sensor chips, with the filled circles representing measurement points where the whole camera image was evaluated. The filled squares denote measurement points where a region of interest (ROI) was initially selected in advance, i.e. prior to data analysis, within which ROI the evaluation then took place. The latter demands significant requirements in respect of time and computation power, and hence resources, in the evaluation device 156. By contrast, FIGS. 5 and 7 show measurement points for devices 110 according to this disclosure with macro-pixels 146 (filled triangles). The trials were carried out using capillaries 116 with a width of 120 µm. While pixel dimensions of 20×20 µm² were used in the conventional CMOS chips, pixels with dimensions of 30×70 µm² (i.e. 30 µm in the y-direction and 70 µm in the x-direction) were used as macro-pixels 146 according to this disclosure which, as indicated in FIG. 3A, were aligned parallel to the capillary 116 with their longer side.

It emerges from the comparison of the substantially identical FIGS. 6 and 7 that conventional sensor chips with conventional evaluation methods only have reliable results once there are approximately 200 to 250 pixels in the x- and y-directions. By contrast, in devices 110 according to this disclosure with macro-pixels 146, a characteristic minimum already forms once there are approximately 5 pixel columns (the different scales of the vertical axes in FIGS. 7 and 6 should be noted) and small errors can already be recorded in FIG. 7 in the case of less than 5 pixel columns, said errors being comparable to errors which in FIG. 6 only occur once there are approximately 250 pixels. Accordingly, it is also possible, for example, to use 3 pixel columns 160 with great accuracy. In the y-direction, it is likewise possible already to record a very small error in the case of a very small number of pixels or a very small number of pixel rows 158, which error is likewise comparable to the errors occurring in FIG. 4 once there are 200 or 250 pixels. Thus, as emerges from e.g. FIG. 5, it is possible to use optical sensors 144 with 30 macro-pixels 144 in the y-direction, or 30 pixel rows 158, to outstanding effect. In particular, a detailed analysis has shown that optical sensors 144 with 32 pixel rows 158 and 7 pixel columns 160, with pixel dimensions of 30 µm×120 µm, are already sufficient to enable good evaluation.

In this case, it should also be noted in particular that each pixel 146 typically requires a circuit with in each case at least three transistors as a result of the high demands in respect of the photometric measurement accuracies, for example in the case of conventional CMOS techniques. Thus, on a conventional sensor 144, e.g. a CMOS chip, the ratio of photosensitive area to overall area of each pixel including the electronics, i.e. the so-called fill factor, reduces with decreasing size of the pixels 146. In the case of conventional CMOS chips, such as the chips illustrated in FIG. 2A, the fill factor is typically merely between 10% and 30%. By contrast, if use is made of the proposed macro-pixels 146, the fill factor in turn is estimated to increase to over 80%, and so the signal yield is higher and hence the reliability, in particular the signal-to-noise ratio, and/or current requirements are more expedient as result of the option of reducing a light power of the light source 140 while maintaining the same signal quality.

As described above, there can be an automatic identification of the evaluation region 136. In the process, the evaluation region 136 can be determined in both x- and y-directions, or merely in one of these directions. It is particularly expedient for the evaluation region 136 to be determined at least in the y-direction, i.e. perpendicular to the capillary 116 or the image thereof, within the image region 148. Here, the vertical position of the capillary 116 or of the evaluation image region 150 can in particular be recognized using a simple algorithm. In particular, the latter can be based on forming the difference in time for each pixel 146. By way of example, as soon as two or more pixels 144 neighboring one another in the horizontal direction in FIG. 3A experience the same change, i.e. a change which is the same (with the exception of a predetermined tolerance region of e.g. 5% or less), it is then possible to deduce that these pixels 146 are arranged within the evaluation image region 150. In the case of 32 pixel rows 158 and an image section of e.g. 1 mm and a magnification of 1:1 (which is the preferred solution), the above-described capillary width of 120 µm for example corresponds to precisely 4 pixel heights, and so at least one pixel row 158 or in actual fact even at least two pixel rows is/are always lying within the evaluation image region 150, i.e. within the image of the capillary 116, and can thus measure discoloration independently of the edge effects of the capillary 116, which can for example be pressed onto the test field 122.

Furthermore, according to this disclosure, there can optionally be an early recognition of the capillary 116 and/or of the evaluation image region 150 by a starting detectable change on the detection side 134, for example by a starting discoloring and/or shadowing on the detection side 134. Accordingly, it is already possible to deduce the evaluation image region 150 from the starting discoloring before a detection reaction has run its complete course. However, more precise analyses have shown that the capillary 116 can be recognized very early, i.e. optionally even before the actual contact between the sample or the capillary 116 and the test field 122, if, as described above, the detection geometry of the detector 138 is designed such that not only the test field 122 or part thereof with the capillary 116 thereof situated over it are measured, but that additionally a narrow strip at the edge detects the actual capillary 116 without the test field 122. This was described above on the basis of FIG. 1. Such regions, in which an image 154 of the capillary 116 can be recognized outside of the test field 122, are illustrated in FIGS. 2A and 3A. The capillary 116 can be determined in a very simple and reliable fashion in these images. If the image 154 of the capillary 116 is detected, it is thus possible to recognize or determine the region, e.g. the pixel rows 158, of the expected discoloration and hence the evaluation image region 150 by extrapolation toward the right-hand side in FIG. 3A. The advantage of this lies in the fact that a blank value can be measured prior to wetting within the evaluation image region 150, without requiring buffer storage of data. Without this simple capillary detection, it is generally necessary at first to buffer store a complete blank image so that it is possible at a later stage, i.e. when the capillary position is recognized, to use precisely the corresponding row from the blank image to establish the blank value, although this blank image merely still comprises e.g. 32×7=224 pixels 146 or the information therefrom in the case of the macro-pixels.

Figure 8:
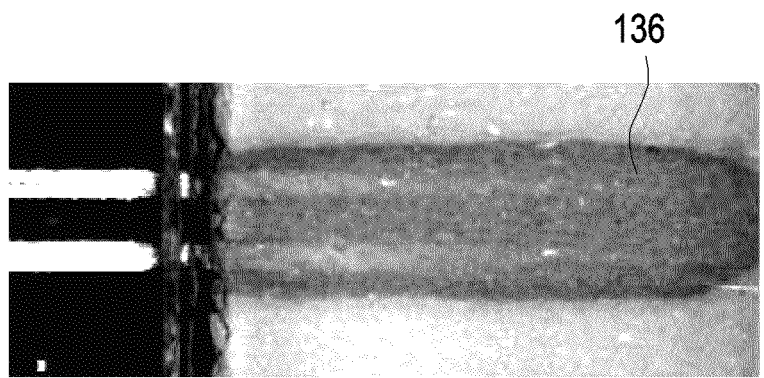
FIGS. 8A to 8C contrast a proper sample transfer (FIG. 8A) and various transfer errors (FIGS. 8B and 8C).
Figure 8:
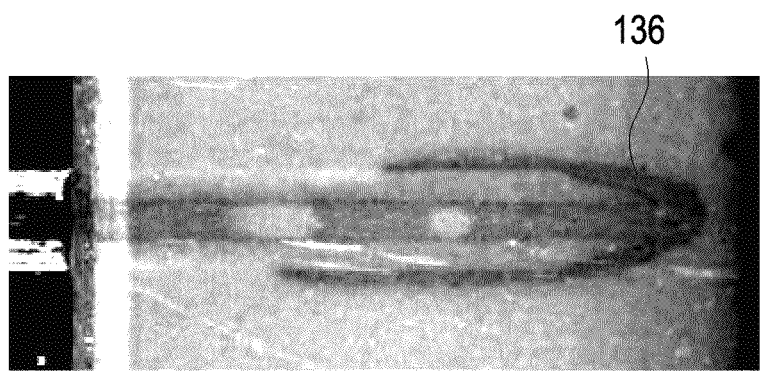
Figure 8:

Furthermore, as described above, the device 110 can also be designed to characterize a transfer of the sample from the microsampler 112 onto the test element 120. In particular, this characterization can be designed such that a correct sample transfer is in the process distinguished from transfer errors or filling errors. This is illustrated in FIGS. 8A to 8C. While FIG. 8A shows correct filling of the capillary 116, followed by a correct transfer onto the evaluation region 136, FIG. 8B shows a case in which the capillary 116 was not filled completely and/or in which there was an incomplete transfer of a sample from the capillary 116 onto the sample application region 130, i.e. under-wetting. By contrast, FIG. 8C shows a case in which there was an overflow, i.e. over-wetting or flooding.

Within the scope of the proposed device 110 with the macro-pixels 146 which can be realized easily from a manufacturing point of view, such errors can be recognized by way of example by means of a simple logic query. Thus, for example, it is possible to carry out a logic query as to whether all pixels 146 within a pixel row 158 have the same grayscale value or the same signal, for example within a narrow error tolerance of e.g. less than 5%. This renders it possible to recognize under-wetting as per FIG. 8B. Furthermore, in order to recognize flooding as per FIG. 8C, it is possible to query whether or not a different grayscale value or a different signal is created after wetting at e.g. 10 pixel rows 158 above the capillary 116 or the image thereof on the optical sensor 144 and/or at a different predetermined offset. By way of example, this would not be the case in the case shown in FIG. 8C. If no deviation is recognized, this makes it possible to infer flooding as per FIG. 8C. However, in principle, it is also possible to use other algorithms for identifying wetting errors.

While exemplary embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SIGNS

110 Device for detecting an analyte
112 Microsampler
114 Lancet element
116 Capillary
118 Drive device
120 Test element
122 Test field
124 Detection layer
126 Separation layer
128 Sample application side
130 Sample application region
132 Approach device
134 Detection side
136 Evaluation region
138 Detector
140 Light source
142 Optical unit
144 Optical sensor
146 Pixel
148 Image region
150 Evaluation image region
152 Image of the lancet element
154 Image of the capillary
156 Evaluation device
158 Pixel rows
160 Pixel columns
162 Detector assembly
164 Deflection device

What is claimed is:

1. A device for detecting at least one analyte in a bodily fluid, comprising:
   a test element having a two-dimensional evaluation region; and
   a spatially resolving optical detector having a plurality of pixels, the detector being configured to image at least part of the test element onto an image region and to image at least part of the evaluation region onto an evaluation image region;
   wherein:
      the detector is matched to the test element such that a predetermined minimum number of pixels is provided for each dimension within the evaluation image region;
      the pixels are arranged in a two-dimensional matrix having pixel rows and pixel columns; and
      the pixel rows are arranged substantially parallel to a longitudinal direction of at least one of the evaluation region or the evaluation image region;

further wherein, the device is configured to automatically recognize the evaluation region according to one or more of the following:
   a pattern recognition method, wherein the device comprises at least one element selected from the group consisting of at least one lancet element and at least one capillary, wherein, in the pattern recognition method, the element is recognized and an extrapolation of the element onto the test element is identified as the evaluation region;
   a signal-change method, wherein a region of the test element within which an optically detectable change occurs as a result of a transfer of the bodily fluid onto the test element is identified as the evaluation region.

2. The device as claimed in claim 1, wherein the device is configured such that bodily fluid is transferred onto the test element for detecting the analyte.

3. The device as claimed in claim 1, further comprising a lancet element with a capillary configured to take up bodily fluid, wherein the device is configured to transfer bodily fluid onto the test element by causing the capillary to approach the test element.

4. The device as claimed in claim 1, wherein the detector has a total number of no more than 1000 pixels.

5. The device as claimed in claim 1, wherein the detector has a longitudinal side and a transverse side, wherein the detector has at least 3 pixel rows in the direction of the transverse side and at least 1 pixel column in the direction of the longitudinal side.

6. The device as claimed in claim 1, wherein the evaluation image region comprises at least three pixels.

7. The device as claimed in claim 1, wherein the evaluation image region has a longitudinal side and a transverse side, at least 3 pixel rows being arranged in the direction of the transverse side and at least 1 pixel column being arranged in the direction of the longitudinal side.

8. The device as claimed in claim 1, wherein the pixels have an elongate pixel geometry, wherein the evaluation region has a longitudinal side and a transverse side, wherein the pixels have a length in the direction of the longitudinal direction and wherein the pixels have a width in the direction of the transverse side, wherein the length exceeds the width.

9. The device as claimed in claim 1, wherein the device is configured to characterize a wetting of the test element with the bodily fluid by comparing a plurality of pixels in at least one dimension.

10. The device as claimed in claim 1, wherein the device is configured to recognize a blank value, wherein the blank value is an optical property of at least one of the image region or the evaluation image region, wherein the device is configured to determine the blank value by one or more of the following:
   recording a temporal image sequence wherein at least one pixel arranged within the evaluation region is recognized and an initial value of the pixel is determined from the temporal image sequence and used as blank value;
   an initial value of the pixels of the image region is stored, the evaluation region is established from a temporal image sequence of the pixels, pixels outside of the evaluation region are discarded and at least one initial value of a pixel within the evaluation region is used as blank value;
   the evaluation region is established and at least one pixel from outside of the evaluation region is used as blank value.

11. The device as claimed in claim 3, wherein the evaluation region is a region of the test element in which an optically detectable change occurs as a result of transferring the bodily fluid onto the test element.

12. The device as claimed in claim 3, wherein the capillary has one or more of the following dimensions:
   a width of 50-200 µm; and
   a length of at least 1 mm.

13. The device according to claim 12, wherein the capillary has a width of 90-150 µm.

14. The device according to claim 12, wherein the capillary has a width of 120 µm.

15. The device according to claim 12, wherein the capillary has a length of at least 2 mm.

16. The device according to claim 12, wherein the capillary has a length of 2-4 mm.

17. The device as claimed in claim 4, wherein the detector has a total number of no more than 500 pixels.

18. The device as claimed in claim 4, wherein the detector has a total number of no more than 256 pixels.

19. The device as claimed in claim 5, wherein the longitudinal side is aligned parallel to a capillary of the device and the transverse side is arranged perpendicular to the capillary.

20. The device as claimed in claim 5, wherein the detector has no more than 100 pixel rows in the direction of the transverse side.

21. The device as claimed in claim 5, wherein the detector has 20-50 pixel rows in the direction of the transverse side.

22. The device as claimed in claim 5, wherein the detector has 2-20 pixel columns in the direction of the longitudinal side.

23. The device as claimed in claim 5, wherein the detector has 5-10 pixel columns in the direction of the longitudinal side.

24. The device as claimed in claim 5, wherein the detector has 7 pixel columns in the direction of the longitudinal side.

25. The device as claimed in claim 6, wherein 5-30 pixels are arranged in the evaluation image region.

26. The device as claimed in claim 6, wherein 10 pixels are arranged in the evaluation image region.

27. The device as claimed in claim 7, wherein the longitudinal side is aligned parallel to a capillary of the device and the transverse side is arranged perpendicular to the capillary.

28. The device as claimed in claim 7, wherein the detector has 3-10 pixel rows arranged in the direction of the transverse side.

29. The device as claimed in claim 7, wherein the detector has at least 3 pixel columns arranged in the direction of the longitudinal side.

30. The device as claimed in claim 7, wherein the detector has 3-10 pixel columns arranged in the direction of the longitudinal side.

31. The device as claimed in claim 7, wherein the detector has 7 pixel columns arranged in the direction of the longitudinal side.

32. The device as claimed in claim 8, wherein the longitudinal side is aligned parallel to the capillary and the transverse side is arranged perpendicular to the capillary.

33. The device as claimed in claim 8, wherein the length exceeds the width by at least a factor of 1.3.

34. The device as claimed in claim 8, wherein the length exceeds the width by at least a factor of 1.7.

35. The device as claimed in claim 8, wherein the length exceeds the width by at least a factor of 2.

36. The device as claimed in claim 8, wherein the length exceeds the width by at least a factor of 2.3.

37. The device as claimed in claim 1, wherein the spatially resolving optical unit is configured to image the evaluation region onto the evaluation image region with a magnification of 3:1 to 0.5:1.

38. The device as claimed in claim 37, wherein the spatially resolving optical unit is configured to image the evaluation region onto the evaluation image region with a magnification of 2:1 to 0.8:1.

39. The device as claimed in claim 37, wherein the spatially resolving optical unit is configured to image the evaluation region onto the evaluation image region with a magnification of 1.1:1 to 0.9:1.

40. The device as claimed in claim 37, wherein the spatially resolving optical unit is configured to image the evaluation region onto the evaluation image region with a magnification of 1:1.

41. The device as claimed in claim 9, wherein the device is configured to evaluate the wetting of the test element with the bodily fluid.

42. The device as claimed in claim 9, wherein the characterization is carried out by comparing adjacent pixels of a pixel row aligned parallel to the evaluation region.

43. A method for recognizing an evaluation region of a test element for detecting at least one analyte in a bodily fluid, comprising:
   providing a lancet element with a capillary;
   drawing bodily fluid into the capillary;
   transferring at least a portion of the bodily fluid onto the test element;
   using a spatially resolved optical detector to image at least part of the test element onto an image region;
   imaging at least part of an evaluation region of the test element onto an evaluation image region; and
   automatically recognizing the evaluation region by at least one of:
      a pattern recognition method in which at least one element selected from the group consisting of the lancet element and the capillary is recognized and an extrapolation of the element onto the test element is identified as the evaluation region; or
      a signal-change method in which a region of the test element within which an optically detectable change occurs as a result of the transfer of the bodily fluid onto the test element is identified as the evaluation region.

44. The method according to claim 43, further comprising using the device as claimed in claim 1.

45. A device for detecting at least one analyte in a bodily fluid, comprising:
   a test element having a two-dimensional evaluation region; and
   a spatially resolving optical detector having a plurality of pixels, the detector being configured to image at least part of the test element onto an image region and to image at least part of the evaluation region onto an evaluation image region;
   wherein:
      the detector is matched to the test element such that a predetermined minimum number of pixels is provided for each dimension within the evaluation image region;
      the pixels are arranged in a two-dimensional matrix having pixel rows and pixel columns; and
      the pixel rows are arranged substantially parallel to a longitudinal direction of at least one of the evaluation region or the evaluation image region;
   further wherein the device is configured to recognize a blank value, wherein the blank value is an optical property of at least one of the image region or the evaluation image region, wherein the device is configured to determine the blank value by one or more of the following:
      recording a temporal image sequence wherein at least one pixel arranged within the evaluation region is recognized and an initial value of the pixel is determined from the temporal image sequence and used as blank value;
      an initial value of the pixels of the image region is stored, the evaluation region is established from a temporal image sequence of the pixels, pixels outside of the evaluation region are discarded and at least one initial value of a pixel within the evaluation region is used as blank value;
      the evaluation region is established and at least one pixel from outside of the evaluation region is used as blank value.

46. The device according to claim 45, wherein the device is configured to automatically recognize the evaluation region.

47. The device according to claim 46, wherein the device is configured to automatically recognize the evaluation region according to one or more of the following:
   a pattern recognition method, wherein the device comprises at least one element selected from the group consisting of at least one lancet element and at least one capillary, wherein, in the pattern recognition method, the element is recognized and an extrapolation of the element onto the test element is identified as the evaluation region;
   a signal-change method, wherein a region of the test element within which an optically detectable change occurs as a result of a transfer of the bodily fluid onto the test element is identified as the evaluation region.

48. The device as claimed in claim 45, wherein the detector has a total number of no more than 1000 pixels.

49. The device as claimed in claim 45, wherein the detector has a total number of no more than 500 pixels.

50. The device as claimed in claim 45, wherein the detector has a total number of no more than 256 pixels.

51. The device as claimed in claim 45, wherein the evaluation image region comprises at least three pixels.

52. The device as claimed in claim 51, wherein 5-30 pixels are arranged in the evaluation image region.

* * * * *